United States Patent
Hossainy et al.

(10) Patent No.: US 8,048,442 B1
(45) Date of Patent: Nov. 1, 2011

(54) MODIFIED HEPARIN-BASED COATINGS AND RELATED DRUG ELUTING STENTS

(75) Inventors: Syed F. A. Hossainy, Fremont, CA (US); Ni Ding, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 284 days.

(21) Appl. No.: 12/211,726

(22) Filed: Sep. 16, 2008

(51) Int. Cl.
A61F 2/04 (2006.01)
A61K 31/727 (2006.01)
B05D 1/36 (2006.01)

(52) U.S. Cl. .......... 424/423; 427/201; 427/202; 600/36; 514/56

(58) Field of Classification Search .......... None
See application file for complete search history.

(56) References Cited

U.S. PATENT DOCUMENTS

| | | | |
|---|---|---|---|
| 4,331,697 A | 5/1982 | Kudo et al. | |
| 5,069,899 A | 12/1991 | Whitbourne et al. | |
| 5,236,570 A | 8/1993 | Ma et al. | |
| 5,270,046 A | 12/1993 | Sakamoto et al. | |
| 5,270,064 A | 12/1993 | Shultz | |
| 5,453,171 A | 9/1995 | Ma et al. | |
| 5,741,881 A | 4/1998 | Patnaik | |
| 5,756,553 A | 5/1998 | Iguchi et al. | |
| 5,770,563 A | 6/1998 | Roberts et al. | |
| 5,855,618 A | 1/1999 | Patnaik et al. | |
| 6,039,977 A | 3/2000 | Venkatraman et al. | |
| 6,042,875 A | 3/2000 | Ding et al. | |
| 6,589,943 B2 | 7/2003 | Byun et al. | |
| 6,630,580 B2 | 10/2003 | Tsang et al. | |
| 6,632,446 B1 | 10/2003 | Hubbell et al. | |
| 7,396,541 B2 | 7/2008 | Hossainy et al. | |
| 7,563,780 B1 | 7/2009 | Hossainy et al. | |
| 2001/0029351 A1 | 10/2001 | Falotico et al. | |
| 2004/0024450 A1* | 2/2004 | Shulze et al. | 623/1.42 |
| 2005/0209688 A1 | 9/2005 | Falotico et al. | |
| 2005/0233062 A1* | 10/2005 | Hossainy et al. | 427/2.1 |
| 2005/0266038 A1* | 12/2005 | Glauser et al. | 424/423 |
| 2006/0014720 A1* | 1/2006 | Hossainy et al. | 514/56 |
| 2008/0124372 A1 | 5/2008 | Hossainy et al. | |

OTHER PUBLICATIONS

"Heparin Coated Blood Oxygenators" (2006). http://biomed.brown.edu/Courses/BI108/2006-108websites/group01Heparin-coatedOxygenators/pages/Biointeractions.htm.*
U.S. Appl. No. 10/871,658, filed Jun. 18, 2004, Hossainy et al.
"SurModics' PhotoLink® Coating Technology", manufacturing process, Abstract 1 pg. downloaded from www.surmodics.com/pageDetail.aspx?pageId, Apr. 8, 2008.
Bajpai et al., "Preparation and characterization of biocompatible spongy cryogels of poly(vinyl alcohol)-gelatin and study of water sorption behaviour", Polymer International vol. 54, No. 9, Abstract 1 pg. (1991).
Biba-Hepcoat, product description, Abstract 2 pgs. downloaded from www.bionteractions.couk/main.asp?id=166, Apr. 11, 2008.
Hatakeyema et al., "Gel-sol transition of poly(vinyl alcohol) hydrogels formed by freezing and thawing", Abstract, Thermochimica Acta, vol. 431, issues 1-2, 1 pg. (2005).
Machida et al., "A structural study of water in a poly(vinyl alcohol) gel by $^{17}$O NMR spectroscopy" J. of Molecular Structure vol. 554, No. 1, Abstract 1 pg. (2000).
Ricciardi et al., "Investigation of the Crystallinity of Freeze/Thaw Poly(vinyl alcohol) Hydrogels by Different Techniques", Macromolecules vol. 37, Abstract 1 pg. (2004).
Lazzeri, et al. "Physico-chemical and mechanical characterization of hydrogels of poly(vinyl acohol) and hyaluronic acid." Journal of Materials Science: Materials in Medicine 5: 862-867 (1994).
Peppas, et al. "Reinforced uncrosslinked poly (vinyl alcohol) gels produced by cyclic freezing-thawing processes: a short review." Journal of Controlled Release 16: 305-310 (1991).
Scully, et al. "Effect of a heparan sulphate with high affinity for antithrombin III upon inactivation of thrombin and coagulation Factor Xa." Biochem. J. 262, 651-658 (1989).

* cited by examiner

*Primary Examiner* — Robert A Wax
*Assistant Examiner* — Danah Al-Awadi
(74) *Attorney, Agent, or Firm* — Squire, Sanders & Dempsey (US) LLP

(57) ABSTRACT

Systems comprising modified heparin-based coatings to form coatings on medical devices are provided. The systems improve the suitability of the heparin-based coatings.

12 Claims, No Drawings

MODIFIED HEPARIN-BASED COATINGS AND RELATED DRUG ELUTING STENTS

FIELD OF INVENTION

The present invention relates to implantable medical devices and coatings for implantable medical devices which include heparin, and methods of coating implantable medical devices.

BACKGROUND

Blood coagulates by the action of its various components in blood when it contacts foreign matter. Hence, there is need for a high anticoagulant property in materials used for the components of medical articles or instruments, such as artificial hearts, artificial cardiac valves, artificial blood vessel, blood vessel catheters, cannulas, pump-oxygenators, blood vessel by-pass tubes, intraaortic balloon pumping, transfusion instruments and extracorporeal circulation circuits, on the portions that contact blood.

Heparin has been commonly used to provide these medical devices anticoagulant properties, but systemic use of heparin may undesirably lead to the formation of a large number of bleeding sites. Methods have been developed to minimize side effects associated with the use of heparin with limited success (see, for example, U.S. Pat. Nos. 5,270,064 and 6,630,580). Meanwhile, problems associated with systemic drug administration have led to the development of methods for local delivery of the drug. Administering a pharmacologically active drug directly to a patient may lead to undesirable consequences because many therapeutic substances have undesirable properties that present pharmacological, or pharmacokinetic barriers in clinical drug application.

Thus, it is desirable to provide for the deliver of heparin locally from an implantable medical device. In addition, it is desirable to deliver other drugs from such an implantable medical device. Therefore, in the art of drug-delivery implantable medical devices, there is a need for an implantable medical device that has heparin at the surface, and that is also capable of delivering a drug that is not heparin.

SUMMARY

Various aspects of the present invention include an implantable medical device including a device body having an outer surface and a first coating layer disposed over the outer surface of the device body. The first coating layer includes a hydrophobic polymer. A second coating layer is disposed over the outer surface of the device body above the first coating layer. The second coating layer includes a glycosaminoglycan which is covalently bound to at least one coating material, a second drug which is not a glycosaminoglycan, and either at least one hydrophobic polymer or at least one amphiphile. The coating material in the second coating layer to which the glycosaminoglycan is bound is not the second drug, and there are no coating layers above the second coating layer.

In an aspect of the invention, the thickness of the first coating layer is between 100 nm and 5 µm.

In an aspect of the invention, the first coating layer further comprises a drug.

In an aspect of the invention, the drug in the first coating layer is micronized heparin or a heparin based material. In another aspect, the heparin based material is micronized.

In an aspect of the invention, the first coating layer further comprises polyethylene glycol, or polyvinylpyrrolidone.

In an aspect of the invention, the second drug in the second coating layer is ionic and the second coating layer further comprises an ionic component to bind with the second drug.

In an aspect of the invention, the ionic component is selected from the group consisting of poly(acrylic acid), poly(L-lactic acid), transamidated poly(acrylamide), copoly(ethylene glycol-dimethylaminoethyl methacrylate), benzoic chloride, tridodecylmethylammonium chloride, and combinations thereof.

In an aspect of the invention, the second coating layer comprises a hydrophobic polymer selected from the group consisting of poly(ethylene-co-vinyl acetate), poly(ethylene-co-vinyl alcohol), a poly(ester-amide), poly(butyl methacrylate) (PBMA), poly(L-lactide), poly(D-lactide), poly(D,L-lactide), poly(D,L-lactide-co-glycolide), acrylates such as, without limitation, poly(methyl methacrylate), poly(n-butyl methacrylate), poly(methylmethacrylate), and fluoropolymers such as, without limitation, poly(vinylidene fluoride) ("PVDF"), poly(vinylidene fluoride-co-hexafluoropropene) ("PDVF-HFP"), poly(tetrafluoroethylene) ("PTFE," or TEFLON®), fluorinated poly(ethylene-co-propylene) ("FEP"), poly(hexafluoropropene), poly(chlorotrifluoroethylene) ("PCTFE"), poly(vinylidene fluoride-co-tetrafluoroethylene) ("PVDF-TFE"), poly(tetrafluoroethylene-co-hexafluoropropene), poly(tetrafluoroethylene-co-vinyl alcohol), poly(tetrafluoroethylene-co-vinyl acetate), poly(tetrafluoroethylene-co-propene), poly(hexafluoropropene-co-vinyl alcohol), poly(tetrafluoroethylene-co-fluoromethylvinyl ether), poly(ethylene-co-tetrafluoroethylene) ("ETFE"), poly(ethylene-co-hexafluoropropene), poly(vinylidene fluoride-co-chlorotrifluoroethylene), fluorinated silicones, perfluoroalkyl vinyl ether and tetrafluoroethylene co-polymer ("PFA"), a co-polymer of vinylidenedifluoride, hexafluoropropylene and tetrafluoroethylene ("TFB"), polyvinylfluoride ("PVF"), a copolymer of poly(tetrafluoroethylene) and fluoromethylvinyl ether, poly(vinylidene fluoride-co-chlorotrifluoroethylene), poly(vinylidene fluoride-co-ethylene), poly(vinylidene fluoride-co-tetrafluoroethylene), poly(tetrafluoroethylene-co-ethylene), poly(vinylidene fluoride-co-trifluoroethylene) ("PVDF-TrFE"), poly(vinylidene fluoride-co-tetrafluoroethylene), and combinations thereof.

In an aspect of the present invention, the second coating layer comprises an amphiphile, and wherein the hydrophobic group of the amphiphile is selected from the group consisting of a fluorocarbon, poly(dimethylsiloxane), a long chain alkyl such as a straight chain alkyl of 8 to 20 carbons, or combinations thereof. The hydrophilic group of the amphiphile is selected from the group consisting of polyethylene glycol, poly(vinyl pyrrolidone), poly(vinyl alcohol), poly(ethylimine), poly(acrylic acid), poly(hydroxyethyl methacrylate), poly(acrylamide), carboxy-methylcellulose, hyaluronic acid, an oligopeptide, poly(L-lactide), phosphorylcholine, heparin, and combinations thereof.

In an aspect of the present invention, the second drug in the second coating layer is a rapamycin or a derivative of rapamycin.

In an aspect of the present invention, the second drug is everolimus.

In another aspect, the second drug is zotarolimus.

An aspect of the present invention is a coating solution, the solution comprising a glycosaminoglycan which is covalently bound to at least one coating material, a second drug that is not a glycosaminoglycan, a hydrophobic polymer, and a good solvent for the hydrophobic polymer.

In an aspect of the invention, the glycosaminoglycan is heparin and/or a heparin-based material.

In an aspect of the invention, the hydrophobic polymer is selected from the same group outlined above that may be added to the second coating layer.

In an aspect of the invention, the good solvent is selected from the group consisting of acetone, methyl ethyl ketone, dimethyl acetamide, dimethyl chloride, n-methylpyrrolidone, tetrahydrofuran (THF), dimethyl sulfoxide (DMSO), toluene, methyl chloroform, and combinations thereof.

An aspect of the present invention is a method to control drug release including the operations of: applying a first coating to an implantable medical device, the first coating including a drug and a polymer; exposing the coated device to a temperature ramp and cool cycle such that the drug crystallinity in the first coating is increased. The temperature ramp and cool cycle is a temperature ramp from a temperature below the drug melting point by at least 10° C. to a temperature above the drug melting point by at least 5° C. over 10-100 minutes and a temperature cool from a temperature above the drug melting point by at least 5° C. to a temperature below the drug melting point by at least 10° C. over less than 5 minutes.

An aspect of the present invention is a method to control drug release including the operations of: applying a first coating to an implantable medical device, the first coating including a drug and a polymer wherein the polymer is capable of physical cross-linking with a temperature change; and exposing the coated device to a temperature ramp and cool cycle such that the extent of physical cross-linking of the polymer in the first coating is increased. The temperature cycle is a freezing cycle obtained by holding the temperature in the range of −10° C. to −35° C. for one (1) to 24 hours, and then thawing at a temperature in the range of +5° C. to +10° C. for one (1) to 24 hours.

In an aspect of the present invention, the polymer in the aspect of the previous paragraph is selected from the group consisting of hyaluronic acid, poly(vinyl alcohol), and combinations thereof.

An aspect of the invention is a method of applying multiple coating layers to an implantable medical device including the steps of: applying a first coating layer comprising a polymer to the device; and applying a second coating layer over the first coating layer. The first coating layer is exposed to a good solvent for the polymer of the first coating layer before and/or during the application of the second coating layer.

In an aspect of the invention, the exposure of the first coating layer to a good solvent for the polymer of the first coating layer is a brief contact time, that is from one (1) second up to 5 minutes, between the good solvent and the first coating layer. In an aspect of the invention, the exposure of the first coating layer to a good solvent for the polymer of the first coating layer occurs simultaneously with the application of the second coating layer, and the coating solution utilized for coating the second layer comprises the good solvent.

In an aspect of the invention, the exposure of the first coating layer to a good solvent for the polymer of the first coating layer occurs simultaneously with the application of the second coating layer, and the application of the second coating layer occurs in an environment saturated with vapor from the good solvent.

An aspect of the invention is a method of applying multiple coating layers to an implantable medical device including the operations of: applying a first coating layer comprising a polymer to the implantable medical device; applying a tie coating layer onto the first coating layer on the implantable medical device, the tie coating layer comprising the polymer of the first layer and one or more of the group consisting of polyethylene glycol, polyvinyl pyrrolidone, and a poly(butyleneterephthalate-co-ethylene glycol) surfactant; and applying a second coating layer over the tie coating layer.

In an aspect of the invention, the implantable medical device is a stent.

DETAILED DESCRIPTION

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless it is expressly stated or obvious from the context that such is not intended.

As used herein, unless specified otherwise, any words of approximation such as without limitation, "about," "essentially," "substantially" and the like mean that the element so modified need not be exactly what is described but can vary from the description by as much as ±15% without exceeding the scope of this invention.

As used herein, "optional" means that the element modified by the term may or may not be present.

As used herein, a "polymer" is a molecule made up of the repetition of a simpler unit, herein referred to as a constitutional unit. The constitutional units themselves can be the product of the reactions of other compounds. A polymer may comprise one or more types of constitutional units. As used herein, the term polymer refers to a molecule comprising 2 or more constitutional units. An "oligomer" on the other hand refers to a molecule comprising less than 20 constitutional units and is a subset of polymers as defined herein. Polymers may be straight or branched chain, star-like or dendritic, or one polymer may be attached (grafted) onto another. Polymers may be cross-linked to form a network.

As used herein, "copolymer" refers to a polymer which includes more than one type of constitutional unit.

As used herein, "biocompatible" when used in reference to polymers, coatings, or other materials referenced herein, means that such a polymer, coating, or material, in its intact, that is as synthesized state, and in its decomposed state (if it decomposes under physiological conditions), i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, the terms "biodegradable", "bioerodable", and "bioabsorbable" as well as degraded, eroded, absorbed, and dissolved, when used in reference to polymers, coatings, or other materials referenced herein, are used interchangeably, and refer to polymers, coatings, and materials that are capable of being completely, or substantially completely (about 80% or more), degraded, dissolved, and/or eroded over time when exposed to physiological conditions (pH, temperature, and fluid or other environment), and can be gradually resorbed, absorbed and/or eliminated by the body, or that can be degraded into fragments that can pass through the kidney membrane of an animal (e.g., a human). Conversely, a "biostable" polymer, coating, or material, refers to a polymer, coating or material that is not biodegradable.

As used herein, a "hydrophobic polymer" is one for which absorption of water, for water at a pH between about 6.0 and 7.5 and at a temperature of 37° C. and at normal atmospheric pressure, is not more than 5% by weight.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, cerebrospinal fluid shunts, and intrauterine devices.

As used herein, "device body" refers to an implantable medical device in a fully formed utilitarian state with an outer surface to which no coating or layer of material different from that of which the device is manufactured has been applied. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

A type of implantable medical device is a "stent." A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

A stent used for patency maintenance is usually delivered to the target site in a compressed state and then expanded to fit the vessel into which it has been inserted. Once at a target location, a stent may be self-expandable or balloon expandable.

In addition to the above uses, stents as well as other implantable medical devices may also be employed for the localized delivery of drugs to specific treatment sites in a patient's body. In fact, drug delivery may be the sole purpose of the stent (or other implantable medical device) or the stent may be primarily intended for another use such as those discussed above with drug delivery providing an ancillary benefit.

As used herein, "outer surface" of an implantable medical device, a device body, or a stent, is meant any surface however spatially oriented that is in contact with bodily tissue or fluids. With respect to a stent, the outer surface includes both the abluminal and luminal surfaces.

Implantable medical devices, including stents, may be made of virtually any material, i.e., materials presently known to be useful for the manufacture of implantable medical devices and materials that may be found to be so in the future, may be used with the various embodiments of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof. Implantable medical devices may also be made of polymers that are biocompatible and biostable or biodegradable, the latter term including bioabsorbable and/or bioerodable, or a combination of biostable and biodegradable polymers.

As used herein, an "amphiphile" or "amphiphilic molecule," is one which has two distinct components, differing in their affinity for a solvent, most particularly water. The part of the molecule that has an affinity for water, a polar solvent, is said to be hydrophilic. The part of the molecule that has an affinity for non-polar solvents such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the Critical Micelle Concentration (CMC) is reached, any remaining surfactant molecules will form into spheres, micelles, with the hydrophilic ends of the molecules facing out, that is, in contact with the water forming the micelle corona and with the hydrophobic "tails" facing toward the center of the of the sphere.

As used herein, "alkyl" refers to a straight or branched chain fully saturated (no double or triple bonds) hydrocarbon (carbon and hydrogen only) group. Examples of alkyl groups include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, and cyclohexyl.

As used herein, "therapeutic agent," "drug," "bioactive agent," and "active agent," which will be used interchangeably, refer to any substance that, when administered in a therapeutically effective amount to a patient suffering from a disease or condition, has a therapeutic beneficial effect on the health and well-being of the patient. A therapeutic beneficial effect on the health and well-being of a patient includes, but it not limited to: (1) curing the disease or condition; (2) slowing the progress of the disease or condition; (3) causing the disease or condition to retrogress; or, (4) alleviating one or more symptoms of the disease or condition.

As used herein, a drug also includes any substance that when administered to a patient, known or suspected of being particularly susceptible to a disease, in a prophylactically effective amount, has a prophylactic beneficial effect on the health and well-being of the individual. A prophylactic beneficial effect on the health and well-being of a patient includes, but is not limited to: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; or, (3) preventing or delaying recurrence of the disease or condition after a course of treatment with a therapeutically effective amount of a substance, which may be the same as or different from the substance used in a prophylactically effective amount, has concluded.

As used herein, "therapeutic agent," "drug," "bioactive agent," and "active agent" also refers to pharmaceutically acceptable, pharmacologically active derivatives of those drugs specifically mentioned herein, including, but not limited to, salts, esters, amides, prodrugs, active metabolites, analogs, and the like.

As used herein, the term "heparin" refers to a heparin molecule, a fragment of a heparin molecule such as pentasaccharide, a derivative of heparin or complexed heparin. Heparin derivatives can be any functional or structural variations of heparin. Representative variations include alkali metal or alkaline earth metal salts of heparin, such as sodium heparin (e.g., hepsal or pularin), potassium heparin (e.g., clarin), lithium heparin, calcium heparin (e.g., calciparine), magnesium heparin (e.g., cutheparine), low molecular weight heparin (e.g., ardeparin sodium) with a molecular weight of from about 4,000 to about 5,000 Daltons and high affinity heparin (see, e.g., Scully, et al., Biochem. J. 262:651-658 (1989)). Other examples include heparin sulfate, heparinoids, and heparin having a hydrophobic counter-ion such as tridodecylmethylammonium and benzalkonium.

As used herein, the term "heparin-based material" is used to mean all heparin materials, materials containing heparin, and materials containing molecules or parts of molecules that act similarly to heparin.

As used herein, "glycosaminoglycan" refers to "any of a group of high molecular weight linear polysaccharides with various disaccharide repeating units and usually occurring in proteoglycans, including the chondroitin sulfates, dermatan sulfates, heparan sulfate and heparin, keratan sulfates, and hyaluronic acid." (from Dorland's Medical Dictionary for Health Consumers. ©2007).

As used herein, "solvent" is defined as a substance capable of dissolving or dispersing one or more substances or capable of at least partially dissolving and/or dispersing the substance (s) to form a uniform solution or dispersion at a selected temperature and pressure. A solvent can refer to one compound, or a mixture of compounds. A solvent can be a fluid.

As used herein a "good solvent," when used in reference to a polymer, refers to one in which the solubility, at the temperature and pressure selected, is at least 10 mg/ml.

As used herein, a material that is described as a layer or a film (e.g., a coating) "disposed over" an indicated substrate refers to, e.g., a coating of the material deposited directly or indirectly over at least a portion of the surface of the substrate. Direct depositing means that the coating is applied directly to the surface of the substrate. Indirect depositing means that the coating is applied to an intervening layer that has been deposited directly or indirectly over the substrate. A coating is supported by a surface of the substrate, whether the coating is deposited directly, or indirectly, onto the surface of the substrate. The terms "coating", "layer", and "coating layer" will be used interchangeably and refer to a layer, film, or coating as described in this paragraph. Unless the context clearly indicates otherwise, a reference to a coating, layer, or coating layer refers to a layer of material that covers all, or substantially all, of the surface, whether deposited directly or indirectly.

One typical but non-limiting manufacturing process for coating a substrate is dissolving or dispersing a polymer, optionally with other additives and/or a drug, in a solvent (where the solvent is a fluid), and disposing the resulting coating solution over the substrate by procedures such as spraying or immersing the substrate in the solution. Such coating procedures are well-known in the art.

After the solution has been disposed over the substrate, the solvent is removed, or substantially removed, by evaporation. When the solvent is removed, what is left is the solid material which forms a layer, film, or coating on the surface of the substrate, either directly or indirectly. The process of drying can be accelerated if the drying is conducted at an elevated temperature, and/or with the addition of a flow of air (or the flow of another gas, especially an inert gas, or a supercritical fluid) over or past the device to enhance mass transfer of the solvent. The coating layer left may include residual solvents as removal of absolutely all of the solvent is generally not possible. Covalent bonding to the material in the coating layer to the substrate below, or to another coating layer below the newly applied layer, is not required. The material forming the coating layer may be broadly referred to as "coating material." As used herein, "coating material" refers to the material of which a coating layer is comprised except that incidental residual solvents are not included in the coating materials.

As used herein, "above" a surface or layer is defined as further from the substrate measured along an axis normal to a surface, or over a surface or layer, but not necessarily in contact with the surface or layer.

As used herein, "below" a surface or layer is defined as closer to the substrate measured along an axis normal to a surface, or under a surface or layer, but not necessarily in contact with the surface or layer.

As used herein, a "primer layer" refers to a coating consisting of a polymer, blend of polymers, and/or other materials that exhibit good adhesion characteristics with regard to the material of which the substrate is manufactured and good adhesion characteristic with regard to whatever material is to be coated on the substrate. Thus, a primer layer serves as an adhesive intermediary layer between a substrate body and materials to be carried by the substrate and is, therefore, applied directly to the substrate.

As used herein, "drug reservoir layer" refers either to a layer of one or more drugs applied neat, or applied with a carrier, or to a layer of polymer or blend of polymers that has dispersed within its three-dimensional structure one or more drugs. A polymeric drug reservoir layer is designed such that, by one mechanism or another, e.g., without limitation, by elution or as the result of biodegradation of the polymer, the drug is released from the layer into the surrounding environment. Preferred drug reservoir layers of the various aspects of the present invention are those including a drug and a polymer.

As used herein, a "heparin coating layer" refers to a coating layer in which heparin, a heparin based material, a glycosaminoglycan, or a material containing a glycosaminoglycan, is present, and is either covalently bound to the substrate, covalently bound to a coating layer on the substrate, or covalently bound to another coating material in the heparin coating layer, such as without limitation, a polymer.

As used herein, "burst release" refers to the uncontrolled release of drug within a very short time, relative to the desired release duration time, after implantation in a patient (animal including a human).

In the discussion that follows, heparin will be used as a representative glycosaminoglycan, but the various aspects of the present invention are not limited to heparin, but encompass the general category of glycosaminoglycans. Furthermore, a stent may be referenced in the various aspects as a representative and non-limiting example of a medical device. However, the various aspects of the present invention are not limited to use with stents, but may be used with any medical device for which a coating is beneficial or desirable.

As noted above, heparin has been commonly used with medical devices to provide medical devices anticoagulant properties. There are several commercially available formulations for coating a surface with heparin, or otherwise providing for heparin at the surface of a device.

One example of a commercially available heparin coating solution is BIBI-HEPCOAT™ from Biointeractions, Ltd., United Kingdom. This formulation contains heparin molecules covalently bound to poly(ethylene oxide) chains. In addition, the formulation contains negatively charged sulfate/sulfonate ion groups. The coating can be used for medical devices. Coatings such as BIBI-HEPCOAT™ will be referred to as heparin type A coating solutions.

Another commercially available means for coating heparin onto a surface of a medical device is APPLAUSE™ HEPARIN COATING from Suromodics, which provides a means to covalently bind heparin to a device surface with PHOTOLINK® technology. The heparin is modified with a photoreactive group. The covalent linkage of the heparin is achieved through hydrogen extraction from the basecoat on the surface of a medical device. Coatings such as APPLAUSE™ HEPARIN COATING which contain heparin to be covalently bound to a substrate to which the coating has been applied will be referred to as heparin type B coating solutions.

Another method for bonding the heparin to a coating, is to have the heparin attach to a polymer or polymeric surface by forming a Schiff base between an amino group and an aldehyde group that heparin and the polymer may have, by forming an amide group between an amine group on a polymer and the carboxyl group on heparin via NHS (N-hydroxysuccinimide) activation. This category includes heparin derivatized with unsaturated groups such as acrylate, e.g., methacrylate, or vinyl alcohol. The heparin functionalized with an unsaturated group can be used in a free radical polymerization to graft or crosslink to a substrate or other formulation components such as, without limitation, a polymer. These functionalized heparin molecules may be included in a heparin type B coating solution if the reaction occurs once the solution is disposed over a substrate. If the functionalized heparin molecules are grafted to another material, such as a polymer first, they may be included in a heparin type A coating solution.

Another method to attach heparin to a surface of a medical device is to coat the device with a biocompatible polymer attached to heparin via a spacer. Heparin can be used as is or used in a modified form. The spacer allows the heparin molecule enough flexibility to allow binding proteins access to the heparin binding sites. Generally, spacers useful for attaching heparin and a polymer have two functional groups, one capable of attaching to heparin, the other capable of attaching to the coating material. A general formula of the spacers can be Y—R—X where X and Y represent the two functional groups and R represents a monomeric, oligomeric, or polymeric di-radical. Exemplary X and Y groups include, but are not limited to, hydroxyl, epoxide, carboxyl, amino, imide, aziridine, thiol, phosphoryl, aldehyde, anhydride, acyl halide, silyl, isocyanate, diisocyanate, carbodiimide, a dihydrazide, a multiaziridine, a multifunctional carbodiimide, a diamine, a primary amine side group on a polymer, N-hydroxy-succinamide, acryloxy terminated polyethylene glycol, methacryloxy terminated polyethylene glycol, and isothiocyanate. Copending U.S. patent application Ser. No. 10/857,141, filed on May 27, 2004, describes this coating more thoroughly and this document incorporates the entire disclosure of U.S. patent application Ser. No. 10/857,141, including any drawings, herein. The heparin molecules attached to a spacer may be incorporated in a heparin type B coating solution.

Methods of derivatizing heparin with hydrophobic materials or polymers are described in, for example, U.S. Pat. Nos. 4,331,697; 5,069,899; 5,236,570; 5,270,046; 5,453,171; 5,741,881; 5,770,563; 5,855,618; 6,589,943 and 6,630,580, each of which is incorporated by reference as if fully set forth, including any drawings, herein.

In some aspects of the present invention the heparin and modified heparin can attach to any substrate surface, such as a metallic surface, or a polymeric surface. In some aspects of the invention, the substrate surface can be a polymeric coating with or without a drug. Thus, in the heparin type A coating solutions, the heparin molecules may be covalently bound to another material, such as, without limitation, a polymer, but are not covalently bound to the substrate or to a coating previously applied to the substrate. The heparin type B coating solutions contain heparin that has been functionalized such that it can be covalently bound to the substrate which is being coated, or to a coating on the substrate, if the substrate has been previously coated. A "modified heparin coating solution" is one in which additional components have been added to the heparin type A or type B coating solutions.

As outlined above, it is desirable to have a heparin coating on a medical device that can also provide for delivery of a second (non-heparin) drug. Thus, an aspect of the invention is an implantable medical device including a coating containing heparin or a heparin based material covalently bound to either the device surface, or more preferably, covalently bound to a coating material. The coated device also provides for delivery of another drug that is not heparin.

There are a number of methods to accomplish the dual delivery of heparin and a second drug. In one aspect of the present invention, the second drug is added to a pre-existing layer on the stent, such as, without limitation, a drug reservoir layer (which may be in direct contact with the substrate and effectively functions as a primer layer), above which the heparin coating is applied. However, a drug reservoir layer in direct contact with the substrate may be limited in the weight or volume percent of drug that may be added as a primer layer generally functions to enhance attachment to the surface of the substrate, such as a device. The heparin type A coating solution may be one that is commercially available such as those discussed above, or those which are developed in the future. In one aspect of the present invention the thickness of the primer layer, or layer applied directly to the substrate, is increased from 100 nm to 1-2 μm to a thickness in the range of about 1-2 μm to about 5 μm. A preferred thickness of the drug reservoir layer adjacent to the surface of the device which functions as a primer is in the range of about 1 to about 5 μm. The increased thickness of the drug reservoir primer layer allows for the inclusion of the second drug while still maintaining adhesion to the surface of the device.

In another aspect of the present invention, an available heparin type A coating solution, such as without limitation, the BIBI-HEPCOATT™ described above, may be modified such that a stent may be coated with a heparin coating layer that includes both heparin and a second drug that is not heparin. In one aspect, a second drug which is not heparin may be added to the heparin type A coating solution, whether commercial or otherwise. If the second drug is hydrophobic, a hydrophobic polymer along with a good solvent for the chosen hydrophobic polymer may be added to the heparin type A coating solution. It is preferred that the solvent added is miscible with the heparin solution which is an aqueous based solution. The addition of the hydrophobic polymer allows for miscibility of the second drug in the heparin coating layer, as well as for controlled release of the second drug and potentially the heparin. In addition, the hydrophobic polymer and the good solvent may also allow the second drug to remain dissolved, dispersed, or substantially dispersed, in the modified coating solution during the time it is applied to the stent. Exemplary, but not limiting, second drugs include rapamycin and rampamycin derivatives such as everolimus, zotarolimus, and sirolimus. In some aspects, the pre-existing coating layer includes a hydrophobic polymer and thus the addition of a hydrophobic polymer to the heparin coating layer improves the adhesion between the two layers.

Exemplary hydrophobic polymers include poly(ethylene-co-vinyl acetate), poly(ethylene-co-vinyl alcohol), poly(butyl methacrylate) ("PBMA"), poly(L-lactide), poly(D-lactide), poly(D,L-lactide), poly(D,L-lactide-co-glycolide), acrylates such as, without limitation, poly(methyl methacrylate), poly (n-butyl methacrylate), poly(methylmethacrylate), and fluoropolymers such as without limitation include poly(vinylidene fluoride) ("PVDF"), poly(vinylidene fluoride-co-hexafluoropropene) ("PDVF-HFP"), poly (tetrafluoroethylene) ("PTFE," or TEFLON®), fluorinated poly(ethylene-co-propylene) ("FEP"), poly(hexafluoropropene), poly(chlorotrifluoroethylene) ("PCTFE"), poly(vinylidene fluoride-co-tetrafluoroethylene) ("PVDF-TFE"), poly(tetrafluoroethylene-co-hexafluoropropene), poly(tetrafluoroethylene-co-vinyl alcohol), poly(tetrafluoroethylene-co-vinyl acetate), poly(tetrafluoroethylene-co-propene), poly(hexafluoropropene-co-vinyl alcohol), poly(tetrafluoroethylene-co-fluoromethylvinyl ether), poly(ethylene-co-tetrafluoroethylene) ("ETFE"), poly(ethylene-co-hexafluoropropene), poly(vinylidene fluoride-co-chlorotrifluoroethylene), fluorinated silicones, perfluoroalkyl vinyl ether and tetrafluoroethylene co-polymer ("PFA"), a co-polymer of vinylidenedifluoride, hexafluoropropylene and tetrafluoroethylene ("TFB"), polyvinylfluoride ("PVF"), a copolymer of poly(tetrafluoroethylene) and fluoromethylvinyl ether, poly(vinylidene fluoride-co-chlorotrifluoroethylene), poly(vinylidene fluoride-co-ethylene), poly(vinylidene fluoride-co-tetrafluoroethylene), poly (tetrafluoroethylene-co-ethylene), poly(vinylidene fluoride-co-trifluoroethylene) ("PVDF-TrFE"), and poly(vinylidene fluoride-co-tetrafluoroethylene). Another class of hydrophobic polymers are the poly(ester-amides) which are polymer that have in their backbone structure both ester and amide bonds. The poly(ester-amide) polymers may be conjugated to the second drug, to the heparin, or to a third drug. Poly (ethylene-co-vinyl alcohol) polymers may contain some poly (vinyl acetate) groups, up to about 5 mole % of other monomers. Any combination of the above hydrophobic polymers may be used.

If the second drug is hydrophilic, a hydrophilic polymer may be added to modify the heparin type A coating solution.

The molecular weight of the hydrophobic or hydrophilic polymer added to the heparin type A coating solution is in the range of 10,000 to 1,000,000 Daltons, preferably 12,000 to 250,000 Daltons, and more preferably, 15,000 to 150,000 Daltons.

The range in weight percent of the hydrophilic or hydrophobic polymer in the heparin coating layer is 2 to 50 weight percent, preferably 5 to 40 weight percent, and more preferably from 5 to 30 weight percent. With respect to the second drug, the range in the weight percent in the heparin coating layer is from 0.1 to 65 weight percent, preferably 1 to 50 weight percent, and more preferably from 2 to 40 weight percent.

In other aspects of the present invention, the heparin type A coating solution may be modified by the addition of an amphiphile as well as the second drug. The amphiphile will migrate, or "bloom," to the surface of the coating because the hydrophobic parts of the amphiphile preferentially orient at the air-coating interface. Thus, in some aspects, the heparin coating layer comprises a thin layer of the amphiphile on the surface. Similarly, to the case outlined above, the addition of the amphiphile to the coating solution may help maintain the drug, and optionally any hydrophobic polymer or other hydrophobic materials that may be added, in solution or dispersed during the coating process. The amphiphile in the coating layer may impact the release, if the second drug is hydrophobic, by limiting the amount of the hydrophobic second drug which is at the surface of the heparin coating. In addition, the amphiphile may increase the solubility of the second drug in the heparin coating layer.

With respect to the addition of an amphiphile, the hydrophobic group of the amphiphile may be chosen from the group consisting of a fluorocarbon, poly(dimethyl siloxane), a straight chain alkyl of 8 to 20 carbons, and combinations thereof. The hydrophilic group of the amphiphile may be selected from the group consisting of polyethylene glycol, poly(vinyl pyrrolidone), poly(vinyl alcohol), poly(ethylimine), poly(acrylic acid), poly(hydroxy ethyl methacrylate), poly(acrylamide), carboxy methyl cellulose, heparin, hyaluronic acid, an oligopeptide, poly(L-lactide), phosphorylcholine, and combinations thereof. In particular, hyaluronic acid has biobeneficial effects in addition to its potential advantages as part of an amphiphile.

The range in the weight percent of the amphiphile in the modified heparin coating solution, that is a modification of the heparin coating solution, is from 0.01 to 10 weight percent, preferably 0.1 to 5 weight percent, and more preferably from 1 to 3 weight percent. For the resulting heparin coating layer, the range in weight percent of the hydrophobic polymer in the coating layer including heparin is 0.5 to 20 weight percent, preferably 1 to 10 weight percent, and more preferably from 2 to 5 weight percent.

Various aspects of the present invention also encompass the addition of an ionic component to the heparin coating solution. The ionic component then may electrostatically bind to the second drug if the second drug is ionicly charged as opposed to neutral. The ionic component may be the heparin molecule itself, or it may be another compound. Non-limiting examples are benzoic chloride, and tridodecylmethyl-ammonium chloride. Other non-limiting exemplary ionic components include poly(acrylic acid), poly(L-lactic acid), transamidated poly(acrylamide) and copoly(ethylene glycol-dimethylaminoethyl methacrylate) (PEG-PD-MAEM). Without being bound by theory, it is believed that the ionic binding of the second drug results in a slower release rate from the heparin coating layer.

The range in the weight percent of the ionic component in the heparin coating layer is from 1 to 70 weight percent, preferably 10 to 60 weight percent, and more preferably from 20 to 30 weight percent.

The above modifications are not only applicable to the heparin type A coating solutions, including without limitation BIBI-HEPCOAT,™ but also the heparin type B coating solutions. However, with the modifications to the heparin type B coating solutions, one must take into account the impact the reaction of the heparin and/or other materials with the substrate surface (which may be either coated or uncoated) may have on the additives.

Thus, an aspect of the invention is an implantable medical device including a coating containing heparin or a heparin based material covalently bound to either the device surface, or a coating on the device surface, and a second drug which is not heparin. Thus, in some aspects a heparin coating such as the APPLAUSET™ HEPARIN COATING from Suromodics, is used to provide the heparin to the device. In such aspects, the heparin is covalently bound to the device surface or a coating on the device surface utilizing the PHOTO-LINK® technology.

In one aspect of the invention, the heparin type B coating solution may be applied over a pre-existing coating, including but not limited to, a drug reservoir layer that is in contact with the substrate and functions as a primer, and which includes the second drug. As outlined above, in other aspects of the invention, the second drug and other polymers and/or other materials may be included with the heparin type B coating solution. In either of the above mentioned aspects, to minimize the degradation of the second drug, the amount of initiator and catalyst utilized in the modified heparin coating solution may be minimized. If a heparin type B coating solution using a photolink is utilized, a longer wavelength may be used for the photolink coupling, which is initiated by exposure to light, so that initiators other than benzophenone derivatives may be used. Preferred alternative initiators include oxybenzone and avobenzone.

As outlined above, in some aspects of the present invention, either the heparin coating solution type A or the heparin coating solution type B may be applied over a pre-existing layer, such as without limitation, a first drug reservoir primer layer. In those aspects, to avoid the premature extraction or release of the drug from the pre-existing layer during the application of the heparin coating, the coating solution may be saturated with the drug of the first drug reservoir layer so that any thermodynamic driving force for drug diffusion from the first drug reservoir layer is significantly reduced or eliminated. In some aspects of the present invention, and depending upon the manner of application of the heparin coating layer, the drug used for saturation of the heparin coating solution may remain behind as part of the heparin coating layer. In other aspects, especially if the coating layer contains heparin which becomes covalently bound to the pre-existing layer as a result of a reaction, the drug-saturated solution may be substantially or completely removed with minimal retention of the drug from the drug-saturated solution in the heparin coating layer.

In those aspects wherein the heparin coating is applied on top of a pre-existing coating, other materials may be added to the pre-existing coating to increase the drug permeability. Non-limiting examples of such additives include polyethylene glycol, and polyvinyl pyrrolidone). In some aspects, the pre-existing coating includes a drug other than heparin, micronized heparin, and/or another micronized drug. In some aspects the heparin-based material may be added and in some aspects, the heparin-based material may be micronized. In such aspects the micronized heparin may act as an additive to increase the permeability of the pre-existing coating. The weight percent of these additives, including micronized heparin and/or another micronized hydrophilic drug may range from 1 weight percent to 40 weight percent in the pre-existing coating layer, preferably from 2 weight percent to 20 weight percent, and more preferably from 3 weight percent to 10 weight percent.

In the various aspects of the present invention, other modifications may be made to the heparin coating layer, or coating solution including heparin, to both modify the mechanical properties of the heparin coating layer, and/or control the release rate of the second drug. The mechanical properties of the heparin layer may not be ideal. If the second drug is hydrophobic, the release of the second drug may be faster than desired since the heparin is hydrophilic, and the second drug may form large domains of a separate phase. If the large domains are at or near the surface of the heparin coating, a large burst release may occur.

One method to reduce the effects of large domains of the second drug is to use smaller crystals of the drug which are more dispersed throughout the coating. Thus, various aspects of the present invention include a method of treatment in which the coated stent is exposed to a temperature ramp and cool cycle and/or a freeze/thaw cycle. It is believed that a temperature ramp will melt the drug crystals, and then cooling down the device will allow for the re-precipitation of the crystals from solution. In particular, a quick freeze cycle may induce many small crystals in the coating layer as the quick temperature change limits crystal growth. The method is particularly applicable to a pre-existing coating, like a drug reservoir primer layer. It is believed that the smaller well-dispersed drug crystals may display a lower tendency to migrate from the pre-existing coating into the heparin coating during the application of the heparin coating. Without being bound by theory, a quick precipitation of drug crystals prevents, or ameliorates, the effect of migration of drug to the surface of the coating. Smaller domains of the second drug separated by the heparin and/or other components are expected to provide a more reproducible release rate with a smaller burst in the drug release.

Also without being bound by theory, it is believed that small drug domains distributed throughout the pre-existing coating may improve mechanical properties. The small drug crystals may act similarly to physical cross-links in the polymer matrix, and as a result the coating may creep less. The improvement in mechanical properties is particularly important for a pre-existing coating that will be exposed to both solvents and high temperature during the application of a second coating. It is believed that a similar improvement in the mechanical properties may be obtained by small crystals of the second drug in the heparin coating layer.

Another means to obtain small drug crystals would be to add a small amount of a non-solvent (such as 0.1 weight percent up to 10 weight percent, or more preferably 0.5 to 5 weight percent) to the coating solution to precipitate the second drug. Thus, some aspects of the present invention include adding a small amount of a non-solvent for the second drug to the modified heparin coating solution, or a coating solution for another coating layer, to precipitate the drug from solution. It is believed that such precipitation may lead to smaller drug crystals and/or smaller drug domains.

A typical temperature range for the temperature ramp and cool and/or temperature freeze and thaw cycle of this invention is from about 10° C. or more below the melting point of the second drug to about to about 5° C. or more above the melting point of the second drug over 1 to 100 minutes, followed by a quench to at least 10° C. below the melting point over 5 minutes or fewer, or in some aspects, in 60 seconds or fewer.

Various aspects of the present invention involve other means to control the release of the second drug from the heparin coating, and/or to improve the mechanical properties of the heparin coating, and/or to limit loss of the drug from a pre-existing coating during the application of the heparin coating. An increase in the diffusion coefficient of a drug through a coating layer may be obtained by the addition of hyaluronic and/or polyvinyl alcohol. Thus, hyaluronic acid and/or poly(vinyl alcohol) may be added to either a first layer applied directly to the substrate, another coating layer, or the heparin coating layer. Both polymers form "hydrogels" in water. The second drug may be blended with a solution of either material in water and cooled to form a gel.

In particular, it has been shown that dissolving poly(vinyl alcohol) in water at an elevated temperature such as about 70° C. to 80° C., and then cooling the solution leads to the formation of a hydrogel. Furthermore, a series of freeze-thaw cycles leads to a gel with improved mechanical properties demonstrated by an increase in the elasticity and increased modulus. The gel re-dissolves when heated to about 70° C. to 80° C., indicating that the gel formed is one which is physically, as opposed to chemically, cross-linked. Several theoretical explanations have been offered for the formation of the gel and the increased gel strength with the freeze-thaw cycles. One explanation is that hydrogen bonding is responsible for the physical cross-links, while other explanations are crystallization of the polymer and/or liquid-liquid separation. It has also been postulated that the freeze-thaw cycles increase the degree of entanglement (Peppas and Stauffer, J. Controlled Release, 16 (1991): 305-310). The addition of hyaluronic acid at 20 weight percent increased the mechanical properties further and demonstrated the highest degree of short-term order in X-ray diffraction for a series of poly(vinyl alcohol)/hyaluronic acid gels. It was hypothesized that hyaluronic acid provided nucleation sites for the poly(vinyl alcohol) crystallization. Hyaluronic acid is added to the solution of poly(vinyl alcohol) after the poly(vinyl alcohol) has been dissolved in the solution and the solution temperature decreased to about 60° C. (Lazzeri et al, Journal of Materials Science: Materials in Medicine, 5 (1994): 862-867).

Depending upon the conditions of formation, poly(vinyl alcohol) hydrogels may exude water over time, or in other words, phase separate. To obtain a stable gel, that is one that does not exude water over time, the gel can be subjected to a freeze-thaw cycle. U.S. Pat. No. 6,039,977 describes processes for obtaining an equilibrium polyvinyl alcohol gel, or a gel of polyvinyl alcohol which is sufficiently close to equilibrium that noticeable changes in the gel (weight loss of about 10% or less) do not occur over a two year time period. The processes utilized depend upon the degree of hydrolysis of the polyvinyl alcohol. U.S. Pat. No. 6,039,977 is incorporated by reference as if fully set forth, including any drawings, herein.

Thus, an aspect of the present invention includes a method of freezing and thawing a coated device wherein a primer layer, another coating layer, or the heparin coating layer, includes hyaluronic acid and/or polyvinyl alcohol. Hyaluronic acid is particularly useful as it is biocompatible and non-thrombogenic. Poly(vinyl alcohol) has also been shown to be biocompatible. Thus, the addition of poly(vinyl alcohol) and/or hyaluronic acid to the modified heparin coating solution, followed by a number of freeze-thaw cycles increases the mechanical properties of the heparin coating layer. The gel may also be used to entrap another drug, and provide for controlled release of the drug.

As a non-limiting example of the above, poly(vinyl alcohol) and/or hyaluronic acid, are added to a coating layer which is a drug reservoir layer, and subjected to a freeze of about −35° C. to −10° C. for about 1 to 24 hours, or more narrowly 1 to 12 hours, or even more narrowly, from 1 to 5 hours. Then the gel is thawed at 5° C. to 10° C., for about 1 to 24 hours, or more narrowly 1 to 12 hours, or even more narrowly, from 1 to 5 hours. Longer time frames for the freeze are generally used for the first cycle. Thus, the freeze-thaw cycle may be repeated a number of times.

In some aspects, poly(vinyl alcohol) and/or hyaluronic acid may be formed into a gel entrapping a drug. The gel may then be divided into small pieces that are blended with a heparin coating solution, preferably a heparin type A coating solution, and therefore become incorporated in the heparin coating layer. The heparin coating layer may optionally be subjected to additional freeze-thaw cycles to assure the gelation (physical cross-linking) of the poly(vinyl alcohol) and/or hyaluronic acid.

Various aspects of the present invention also include methods to increase or provide for adhesion between a heparin coating layer and a pre-existing coating layer, such as, without limitation, a primer layer, or between any two coating layers.

These methods are preferably used with the heparin type A coatings for which the heparin is not covalently bound to the substrate or coating below. One method for accomplishing improved adhesion is the modification of the heparin based coating solution. Addition of a hydrophobic polymer along with a solvent which allows the hydrophobic polymer to be incorporated into solution or an amphiphilic polymer, as previously discussed, may improve adhesion between the layers if the pre-existing layer is primarily hydrophobic as similar materials tend to adhere better than dissimilar materials.

Another method to improve adhesion involves exposing the pre-existing coating layer to a good solvent for the polymer in the pre-existing layer. As a result of being exposed to a good solvent, the polymer swells. In this context, "swelling" means that a number of the polymer chains near the surface of the solid polymer experience a solvent-solute interaction with the applied solvent. This causes portions of the chains to move away from each other, increasing the inter-chain distance of these polymer chains, or in other words, the chains take on a more extended conformation. As a result, during the application of the heparin coating layer on top, there is an increased likelihood of penetration of the solution, including polymers in the solution, into the layer below. When the swelling solvent evaporates, the solid polymer's surface chains return to an unswelled state, and the surface polymer chains of the solid polymer trap some of the material from the heparin coating solution between the chains. Thus, the result is more entanglements between the polymers of the two layers.

The exposure to the solvent may be as a result of inclusion of some of the good solvent in the modified heparin coating solution, or the application of the modified heparin coating solution may occur in an environment comprising a saturated vapor of the good solvent. Another means is by wiping the surface of the coated device with the good solvent, or spraying the good solvent onto the surface of the coated device. The degree of swelling of the polymer at the surface of the coated device depends upon the choice of solvent, the duration of the contact time, and the temperature at which the exposure occurs. In an aspect of the present invention, the exposure of the coated device to the good solvent occurs above, at, or just below (within about 10° C.) the glass transition temperature of the polymer of the pre-existing layer.

Exemplary good solvents for particular polymers that may be used in a pre-existing layer include dimethyl acetamide for ethylene vinyl alcohol copolymer (trade name EVAL), and cyclohexane or acetone for poly (vinylidene fluoride-co-hexafluoropropylene) (PVDF-HFP).

Another method to increase adhesion is to include a "tie" layer, or a layer that joins the other two layers together. The tie layer would include a common component and/or component compatible with each of the adjacent layers. The tie layer would be thin, about 0.5 to 2 μm in thickness. Common or compatible polymer components would be expected to entangle with the adjacent layer, and thus the entanglements with both the pre-existing layer and the heparin coating layer "tie" the two layers together.

As a non-limiting example, a tie layer may contain a combination of the polymer in the pre-existing layer and a hydrophilic component that is miscible with the heparin coating. Non-limiting examples of hydrophilic components include polyvinyl pyrrolidone and polyethylene glycol. In an aspect of the present invention, the tie layer may include in addition to or instead of the hydrophilic component, a poly(butylene-terephthalate-co-ethylene glycol) (PBT-PEG) surfactant (trade name POLYACTIVE® available from IsoTis Corp. of Holland). In various POLYACTIVE compositions, the ratio between the units derived from ethylene glycol and the units derived from butylene terephthalate can be between about 0.67:1 and about 9:1. The molecular weight of the units derived from ethylene glycol can be between about 300 and about 4,000 Daltons.

For those aspects of the invention including a tie layer, control over the degree of diffusion of one coating material into the other coating material, comes from manipulating the amount of PEG, PVP, or surfactant such as POLYACTIVE, or manipulating the molecular weight of the PEG block in the polymer backbone of the POLYACTIVE, manipulating the contact time, or manipulating the temperature, the solvent selection, and combinations of these.

The weight percent of the polymer of the pre-existing layer in the tie layer is from 1 to 50 weight percent, preferably 2 to 40 weight percent, and more preferably from 5 to 15 weight percent. The preferred weight average molecular weight of the polymer of the pre-existing layer which is included in the tie layer is from 20,000 to 500,000 Daltons, preferably 50,000 to 400,000 Daltons, and more preferably from 100,000 to 350,000 Daltons. The weight percent of the hydrophilic component in the tie layer is from 5 to 85 weight percent, preferably 10 to 70 weight percent, and more preferably from 25 to 60 weight percent. The weight average molecular weight of the hydrophilic component, if a polymer, included in the tie layer is from 200 to 500,000 Daltons, preferably 400 to 100,000 Daltons, and more preferably from 1000 to 20,000 Daltons.

The various aspects of the present invention outlined above may be combined to form a number of embodiments of the present invention.

Representative hydrophobic polymers that may be used with the various aspects of the present invention include, but are not limited to, poly(ester-amide), polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly (lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho esters), polyphosphazenes, poly (phosphoesters), poly (tyrosine derived arylates), poly(tyrosine derived carbonates), polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(meth-acrylates) such as poly(butyl methacrylate) (PBMA) or poly (methyl methacrylate) (PMMA), poly(vinyl acetate), poly (ethylene-co-vinyl acetate), poly(ethylene-co-vinyl alcohol), poly(ester urethanes), poly(ether-urethanes), poly(carbonate-urethanes), poly(silicone-urethanes), poly(urea-urethanes) and a combination thereof.

Representative hydrophilic polymers include, but are not limited to, polymers and co-polymers of PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), hydroxyl bearing monomers such as HEMA, hydroxypropyl methacrylate (HPMA), hydroxypropylmethacrylamide, and 3-trimethylsilylpropyl methacrylate (TMSPMA), poly(ethylene glycol) (PEG), poly(propylene glycol), SIS-PEG, polystyrene-PEG, polyisobutylene-PEG, PCL-PEG, PLA-PEG, PMMA-PEG, PDMS-PEG, PVDF-PEG, PLURONIC™ surfactants (polypropylene oxide-co-polyethylene glycol), poly(tetramethylene glycol), poly(L-lysine-ethylene glycol) (PLL-g-PEG), poly(L-g-lysine-hyaluronic acid) (PLL-g-HA), poly(L-lysine-g-phosphoryl choline) (PLL-g-PC), poly(L-lysine-g-vinylpyrrolidone) (PLL-g-PVP), poly(ethylimine-g-ethylene glycol) (PEI-g-PEG), poly(ethylimine-g-hyaluronic acid) (PEI-g-HA), poly (ethylimine-g-phosphoryl choline) (PEI-g-PC), and poly (ethylimine-g-vinylpyrrolidone) (PEI-g-PVP), PLL-co-HA, PLL-co-PC, PLL-co-PVP, PEI-co-PEG, PEI-co-HA, PEI-co-PC, and PEI-co-PVP, hydroxy functional polyvinyl pyrrolidone), polyalkylene oxides, dextran, dextrin, sodium hyaluronate, hyaluronic acid, elastin, chitosan, acrylic sulfate, acrylic sulfonate, acrylic sulfamate, methacrylic sulfate, methacrylic sulfonate, methacrylic sulfamate and combinations thereof.

While particular embodiments and aspects of the present invention have been shown and described, it will be obvious to those skilled in the art that changes and modifications can be made without departing from the embodiments or aspects of this invention in its broader aspects and, therefore, the appended claims are to encompass within their scope all such changes and modifications as fall within the true spirit and scope of the embodiments and aspects of this invention.

What is claimed is:
1. An stent comprising:
a device body having an outer surface;
a first coating layer disposed over the outer surface of the device body comprising a hydrophobic polymer; and
a second coating layer above the first coating layer, the second coating layer comprising a glycosaminoglycan which is covalently bound to at least one coating material, a second drug which is not a glycosaminoglycan, and either at least one hydrophobic polymer or at least one amphiphile;
wherein
the coating material in the second layer to which the glycosaminoglycan is bound is not the second drug;
there are no coating layers above the second coating layer;
the second drug in the second coating layer is ionic; and
the second coating layer further comprises an ionic component to bind with the second drug, the ionic component being copoly(ethylene glycol-dimethylaminoethyl methacrylate).

2. The stent of claim 1, wherein the glycosaminoglycan is heparin or a heparin-based material.

3. The stent of claim 1, wherein the thickness of the first coating layer is between 100 nm and 5 μm.

4. The stent of claim 1, wherein the first coating layer further comprises a drug.

5. The stent of claim 4, wherein the drug in the first coating layer is micronized heparin or heparin-based material.

6. The stent of claim 4, wherein the first coating layer further comprises polyethylene glycol or polyvinylpyrrolidone.

7. The stent of claim 1, wherein the second coating layer comprises a hydrophobic polymer selected from the group consisting of poly(ethylene-co-vinyl acetate), poly(ethylene-co-vinyl alcohol), poly(methyl methacrylate), poly(n-butyl methacrylate), poly(methylmethacrylate), poly(vinylidene fluoride) ("PVDF"), poly(vinylidene fluoride-co-hexafluoropropene) ("PDVF-HFP"), poly(tetrafluoroethylene) ("PTFE"), fluorinated poly(ethylene-co-propylene) ("FEP"), poly(hexafluoropropene), poly(chlorotrifluoroethylene) ("PCTFE"), poly(vinylidene fluoride-co-tetrafluoroethylene) ("PVDF-TFE"), poly(tetrafluoroethylene-co-hexafluoropropene), poly(tetrafluoroethylene-co-vinyl alcohol), poly(tetrafluoroethylene-co-vinyl acetate), poly(tetrafluoroethylene-co-propene), poly(hexafluoropropene-co-vinyl alcohol), poly(tetrafluoroethylene-co-fluoromethylvinyl ether), poly(ethylene-co-tetrafluoroethylene) ("ETFE"), poly(ethylene-co-hexafluoropropene), poly(vinylidene fluoride-co-chlorotrifluoroethylene), fluorinated silicones, perfluoroalkyl vinyl ether, tetrafluoroethylene co-polymer ("PFA"), a co-polymer of vinylidenedifluoride, hexafluoropropylene and tetrafluoroethylene ("TFB"), polyvinylfluoride ("PVF"), a copolymer of poly(tetrafluoroethylene) and fluoromethylvinyl ether, poly(vinylidene fluoride-co-chlorotrifluoroethylene), poly(vinylidene fluoride-co-ethylene), poly(vinylidene fluoride-co-tetrafluoroethylene), poly(tetrafluoroethylene-co-ethylene), poly(vinylidene fluoride-co-trifluoroethylene) ("PVDF-TrFE"), poly(vinylidene fluoride-co-tetrafluoroethylene), a poly(ester-amide), a poly(ester-amide) conjugated to heparin, poly(L-lactide), poly(D-lactide), poly(D,L-lactide), poly(meso-lactide), poly(D,L-lactide-block-ethylene glycol-block-D,L-lactide), poly(meso-lactide-block-ethylene glycol-block-meso-lactide), and combinations thereof.

8. The stent of claim 7, wherein the second drug in the second coating layer is a rapamycin derivative.

9. The stent of claim 7, wherein the second drug in the second coating layer is everolimus.

10. The stent of claim 1, wherein the second coating layer comprises an amphiphile, and wherein the hydrophobic moiety of the amphiphile is selected from the group consisting of a fluorocarbon, poly(dimethyl siloxane), a long chain alkyl, and combinations thereof and the hydrophilic moiety of the amphiphile is selected from the group consisting of polyethylene glycol, poly(vinyl pyrrolidone), poly(vinyl alcohol), poly(ethylimine), poly(acrylic acid), poly(hydroxy ethyl methacrylate), poly(acrylamide), carboxy methyl cellulose, hyaluronic acid, an oligopeptide, poly(L-lactide), heparin, phosphorylcholine, and combinations thereof.

11. The stent of claim 10, wherein the second drug in the second coating layer is a rapamycin derivative.

12. The stent of claim 10, wherein the second drug in the second coating layer is everolimus.

\* \* \* \* \*